United States Patent [19]
King et al.

[11] Patent Number: 5,132,456
[45] Date of Patent: Jul. 21, 1992

[54] SORPTION OF CARBOXYLIC ACID FROM CARBOXYLIC SALT SOLUTIONS AT PHS CLOSE TO OR ABOVE THE $PK_a$ OF THE ACID, WITH REGENERATION WITH AN AQUEOUS SOLUTION OF AMMONIA OR LOW-MOLECULAR-WEIGHT ALKYLAMINE

[75] Inventors: C. Judson King, Kensington; Lisa A. Tung, El Cerrito, both of Calif.

[73] Assignee: The Regents of the University of California, Oakland, Calif.

[21] Appl. No.: 697,315

[22] Filed: May 7, 1991

[51] Int. Cl.$^5$ ............................................. C07C 51/42
[52] U.S. Cl. .................................. 562/593; 562/485; 562/477
[58] Field of Search ........................ 562/593, 485, 477

[56] References Cited

U.S. PATENT DOCUMENTS

| | | | |
|---|---|---|---|
| 2,650,248 | 8/1953 | Collier | 562/593 |
| 2,664,441 | 12/1953 | Owens | 562/593 |
| 2,697,724 | 12/1954 | Collier | 562/593 |
| 2,097,725 | 12/1954 | Bryce | 562/593 |
| 4,250,331 | 2/1981 | Shimshick | 562/593 |
| 4,705,894 | 11/1987 | Su | 562/593 |
| 4,874,700 | 10/1989 | Seipenbusch | 562/593 |
| 4,879,412 | 11/1989 | Iwasaki et al. | 562/593 |
| 4,902,828 | 2/1990 | Wickenhaeuser | 562/593 |

FOREIGN PATENT DOCUMENTS

| | | |
|---|---|---|
| 581194 | 8/1959 | Canada . |
| 3506944 | 10/1985 | Fed. Rep. of Germany . |
| 572473 | 9/1980 | Japan . |
| 7118523 | 7/1982 | Japan . |
| 3005172 | 1/1983 | Japan . |
| 8164541 | 9/1983 | Japan . |

*Primary Examiner*—Paul J. Killos
*Attorney, Agent, or Firm*—Morrison & Foerster

[57] ABSTRACT

Carboxylic acids are sorbed from aqueous feedstocks at pHs close to or above the acids' $pH_a$ into a strongly basic organic liquid phase or onto a basic solid adsorbent or moderately basic ion exchange resin. the acids are freed from the sorbent phase by treating it with aqueous alkylamine or ammonia thus forming an alkylammonium or ammonium carobxylate which dewatered and decomposed to the desired carboxylic acid and the alkylamine or ammonia.

25 Claims, 5 Drawing Sheets

SORPTION OF CARBOXYLIC ACID FROM CARBOXYLIC SALT SOLUTIONS AT PHS CLOSE TO OR ABOVE THE $PK_a$ OF THE ACID, WITH REGENERATION WITH AN AQUEOUS SOLUTION OF AMMONIA OR LOW-MOLECULAR-WEIGHT ALKYLAMINE

ORIGIN OF THE INVENTION

This invention was made in the performance of work funded by the Energy Conservation and Utilization Technology (ECUT) Division and Advanced Industrial Concepts Division of the United States Department of Energy under Contract No. DE-AC03-76SF00098. The United States Government has rights to this invention.

TECHNICAL FIELD

The invention is in the field of chemical engineering. More particularly it relates to improvements in sorption (i.e., solid phase and solvent extraction) processes for recovering carboxylic acid from aqueous streams at pHs close to or above the $pK_a$ of the carboxylic acid.

BACKGROUND OF THE INVENTION

This invention provides a sorbing method for recovering carboxylic acid from aqueous solutions at pHs above the $pK_a$ of the carboxylic acid(s), i.e., under conditions where the carboxylic acid is present in solution largely as a carboxylate salt, and thereafter regenerating the sorbent. Carboxylic acids are important articles of commerce and are among the most attractive chemical products for manufacture from biomass by fermentation. Adipic acid is a large-scale raw material for manufacture of nylon. Citric, acetic, propionic, butyric, lactic, succinic, malic and fumaric acids are other important current and potential products. Most fermentations producing carboxylic acids work best (or work only at all) at solution pHs above the $pK_a$ of the acid, and this invention provides an effective method of recovery and regeneration under these conditions.

Extraction has been a well-established sorbent method for recovery of carboxylic acids. It has also been recognized that there are solid phase sorbents which will take up carboxylic acids effectively. For acids with low volatilities (e.g., dicarboxylic acids and hydroxycarboxylic acids) methods for regenerating extractants and solid sorbents have been limited. Heretofore, the only workable method of using extractants and sorbents strong enough to extract a carboxylic acid from a solution at pH above the $pK_a$ has been back-extraction with an aqueous solution of an inorganic base, such as calcium hydroxide. Recovery of the carboxylic acid then requires addition of a strong acid, such as sulfuric acid, to the aqueous back-extract so as to precipitate calcium sulfate and yield an aqueous solution of carboxylic acid. The result is that both sulfuric acid and calcium hydroxide are consumed and a waste calcium sulfate salt stream is produced.

Electrodialysis with "water-splitting" membranes is also claimed to have the capability of recovering free carboxylic acid from aqueous carboxylate solutions. This approach is still developmental, and no industrial installation is known yet to have been built.

As can be seen from this description of background, various methods used heretofore to recover carboxylic acids have presented limitations and thus offer opportunities for improvement. It is accordingly a general object of the invention to provide an efficient process for the recovery of carboxylic acids from aqueous solutions at pHs close to or above their $pK_a$s which neither consumes large amounts of chemicals nor generates substantial waste chemicals.

REFERENCES

There is a substantial body of art in the area of acid recovery which has been collected by the present inventors in the course of their work. This body of art includes:

Kulprathipanja in U.S. Pat. No. 4,720,579 discloses adsorption of citric acid by styrene-divinylbenzene adsorbents, with regeneration by water or mixture of acetone and water.

U.S. Pat. No. 4,323,702, corresponding to British Patent No. 2,064,526A, discloses adsorption of citric acid by adsorbents containing pyridyl functional groups, with regeneration by leaching with an organic solvent, such as an alcohol or ketone, yielding a relatively dilute organic solutions.

Kulprathipanja and Strong in U.S. Pat. No. 4,924,027 disclose adsorption of citric acid by adsorbents containing tertiary amine or pyridyl functionalities (including Bio-Rad AG3-X4A and AG4-X4), with regeneration by an aqueous solution of sodium, potassium or ammonium hydroxide. It is indicated that the product would be sodium, potassium or ammonium citrate, or that a mineral acid would have to be used to return the citrate to the free citric acid form. This patent and U.S. Pat. No. 4,720,579 are also specifically designated as methods for recovery from acid solution (pH $<pK_a$).

B. Urbas, in U.S. Pat. Nos. 4,405,717 and 4,444,881, teaches a process for recovering acetic acid, lactic acid, butyric acid and citric acid directly from fermentation broths. This process involves converting the acid to a calcium salt and then adding a tertiary amine carbonate (especially tributylamine carbonate) to give a trialkylammonium salt of the acid and calcium carbonate. The trialkylammonium carboxylate is heated to give the acid and the corresponding trialkylamine. This process has the disadvantage that it generates calcium carbonate, a solid waste that needs to be disposed of or heated to high temperatures in a kiln to convert it back to calcium oxide. Also in these patents, there is a preference for higher molecular weight amines and the use of distillation to remove volatile acids from the less volatile amines.

The following additional references are also known to one or more of the present inventors and relate to the general subject matter of the present invention: Baniel, A. M.; Blumberg, R.; Hajdu, K. "Recovery of Acids from Aqueous Solutions". U.S. Pat. No. 4,275,234. Jun. 23, 1981.

Busche, R. M. "The Business of Biomass". *Biotechnol. Progr.* 1985, 1, 165–180.

Cullis, C. F.; Waddington, D. J. "The Gaseous Oxidation of Tertiary Aliphatic Amines, II. Trimethylamine". *Proc. Royal Soc. A* 1958, 246, 91–98.

Holten, C. H. *Lactic Acid: Properties and Chemistry of Lactic Acid and Derivatives.* Verlag Chemie: Copenhagen, 1971.

Jones, P. W.; Gesser, H. D. "Formation of Hydrogen from Amine Oxidation and Pyrolysis". *Combustion and Flame* 1972, 19, 134.

Kaufman, R. G. "The Thermal Decomposition of Trimethylamine". Ph.D. dissertation, The Catholic University of America, Washington DC, 1962.

King, C. J. "Acetic Acid Extraction". In *Solvent Extraction Handbook*; Lo, T. C.; Baird, M. H. I.; Hanson, C., Eds.; Wiley-Interscience: New York, 1983.

Kuo, Y.; Munson, C. L.; Rixey, W. G.; Garcia, A. A.; Frierman, M. "Use of Adsorbents for Recovery of Acetic Acid from Aqueous Solutions. I - Factors Governing Capacity". *Separ. & Purif. Methods* 1987, 16, 31–64.

Lipinsky, E. S.; Sinclair, R. G. "Is Lactic Acid a Commodity Chemical?". *Chem. Eng. Progr.* 1986, 82 (1), 26–32.

Lockwood, L. B. "Production of Organic Acids by Fermentation". In *Microbial Technology*; Peppler, H. J.; Perlman, D., Eds.; Academic: New York, 1979; pp. 356–387.

Mitchell, J. A.; Reid, E. E. "The Preparation of Aliphatic Amides". *J. Am. Chem. Soc.*, 1979, 53, 1879–1883.

Pearson, D. E.; Levine, M. "The Variation of Partition Ratios in Mixed Solvents". *J. Org. Chem.*, 1952, 17, 1356–1360.

Poole, L. J.; King, C. J. 1990. "Regeneration of Amine-Carboxylic Acid Extracts". Report No. LBL-28614; Lawrence Berkeley Laboratory: Berkeley, Cal., 1990.

Sato, M.; Nakahara, T.; Yamada, K. "Fermentative Production of Succinic Acid from n-Paraffin by *Candida brumptii* IFO 0731". *Agric. Biol. Chem.* 1972, 36, 1969–1974.

Starr, J. N., Dept. of Chemical Engineering, Univ. of California, Berkeley, personal communication, 1989.

Streitwieser, A., Jr.; Heathcock, C. H. *Introduction to Organic Chemistry*; Macmillan: New York, 1976; Chaps. 17 & 18.

Tamada, J. A.; Kertes, A. S.; King, C. J. "Extraction of Carboxylic Acids with Amine Extractants. I -Equilibria and Law-of-Mass-Action Modeling". *Ind. Eng. Chem. Res.* 1990, 29, 1319–1326 (1990).

Tamada, J. A.; King, C. J. "Extraction of Carboxylic Acids by Amine Extractants". Report No. LBL-25571; Lawrence Berkeley Laboratory: Berkeley, Cal., 1989.

Tamada, J. A.; King, C. J. "Extraction of Carboxylic Acids with Amine Extractants. III - Effect of Temperature, Water Co-extraction and Process Considerations". *Ind. Eng. Chem. Res.* 1990, 29, 1333–1338 (1990).

Urbas, B. "Recovery of Acetic Acid from a Fermentation Broth". U.S. Pat. No. 4,405,717. Sep. 20, 1983.

Urbas, B. "Recovery of Organic Acids from a Fermentation Broth". U.S. Pat. No. 4,444,881. Apr. 24, 1984.

Weast, R. C. *Handbook of Chemistry and Physics.* 54th ed., CRC: W. Palm Beach Fla., 1974.

Yabannavar, V. M.; Wang, D. I. C., "Bioreactor System With Soluen Extraction for Organic Acid Production," *Ann. N.Y. Acad. Sci.* 1987 (Biochem. E.) 523–535.

DISCLOSURE OF THE INVENTION

We have now found an improved process for recovering carboxylic acids from carboxylic acid-containing aqueous streams which have pHs close to or above the $pK_a$ of the acids. This means that the acids are present predominantly as their carboxylate salts. Viewed as an overall process, the carboxylic acids are first removed from the aqueous stream by a sorption technique, such as a solid-phase adsorption or ion exchange or a liquid-phase extraction. This sorption is carried out at the pH of the aqueous feedstream—that is, a pH which is close to or above the $pK_a$ of the acid being isolated. The sorption employs a strongly basic solid sorbent, a strongly basic liquid extractant or a weak to moderate basicity anion exchanger. The sorbed carboxylic acid is then recovered from the sorbing phase and the sorbing phase is regenerated by contacting the sorbing phase with an aqueous solution of ammonia or a low molecular weight alkylamine. This "back-extracts" the carboxylic acid into the aqueous extraction phase as an ammonium or alkylammonium carboxylate. When this aqueous solution is heated and/or dewatered, the ammonium or alkylammonium carboxylate decomposes to give rise to the carboxylic acid which can then be recovered. The ammonia or alkylamine is also thereby regenerated and can be recycled. Thus, a process is achieved which consumes no significant amounts of chemicals and generates no significant amounts of waste by-product.

It was unexpected that these basic sorbents would, on the one hand, be capable of effectively removing these acids at pHs close to or above their $pK_a$s and, on the other hand, be capable of being facilely regenerated by contact with an aqueous solution of a low molecular weight alkylamine. Although solvent extraction and adsorption are two methods potentially attractive for recovery of carboxylic acids, since they have the capability of selectively removing the desired carboxylic acid product from the complex fermentation mixture with common solvents and adsorbents, these methods have been generally ineffective at pH values substantially above the $pK_a$ of the carboxylic acid. This is because of the high degree of conversion of the acid to the anionic carboxylate at these pHs. We have found, however, that if a strongly basic extractant or sorbent is used, the strong basicity will provide a strong affinity, and therefore a substantial capacity, for the carboxylic acid, even though the concentration of un-ionized carboxylic acid is low. Similarly, a weak to moderately basic anion exchanger (solid or liquid) will take up the carboxylate anion.

Another unexpected finding has been the effectiveness of our regeneration step. The method of regeneration used in the present invention is leaching or back-extraction with an aqueous solution of ammonia or low molecular weight alkylamine, especially trimethylamine (TMA). The resultant aqueous ammonium or alkylammonium carboxylate solution can be concentrated if necessary (e.g., by evaporation of water), and the carboxylate can be decomposed thermally to yield the product carboxylic acid and ammonia or amine, particularly gaseous TMA, which can be condensed and recycled. Thus, the volatility of the TMA base allows the basic back-extractant or leachant to be decomposed and avoids the classical problem of consumption of both a base and acid and disposal of a salt.

We have demonstrated that aqueous ammonia or an aqueous low molecular weight alkylamine serves as a highly effective regenerant for recovering succinic, lactic and fumaric acids from extracts composed of these acids in a solvent composed of highly basic Alamine 336 extractant in methyl isobutyl ketone (MiBK) diluent. (Alamine 336, made by Henkel Corp., is a tertiary amine with 8 to 10 carbon alkyl groups.) Furthermore, we have demonstrated that the resulting aqueous solutions of trimethylammonium carboxylates can be decomposed by heating and stripping of released TMA. For fumaric and succinic acids, this step yields the solid, precipitated carboxylic acid as a TMA-free product. For lactic acid the decomposition is incomplete, being stopped by formation of a viscous, almost glassy mass containing polymerized lactic acid along with substantial TMA and water. There are, however, effective ways of driving the decomposition to completion for lactic acid, such as by diluting the viscous mass with an appropriate solvent (e.g., MiBK) and continuing the heating and decomposition process.

We observed that back-extraction of Alamine 336 with aqueous TMA gave essentially quantitative, stoichiometric recovery. In exploring the reason for this, we found that the cause is the much stronger basicity of alkylamines in the aqueous phase than in the organic phase, resulting from ionization of the amine in the aqueous phase. Indeed, the $pK_a$ of the trimethylammonium ion is 9.8.

It is possible to regenerate extractants and adsorbents of still higher basicity using back-extraction, or leaching, with aqueous ammonia or low molecular weight alkylamines, followed by thermal decomposition of the ammonium or alkylammonium carboxylate. Furthermore, it is possible to use weak- to intermediate-basicity anion exchangers (solid or liquid) to take up the carboxylic acid from aqueous solutions with a pH close to or above the $pK_a$ of the carboxylic acid, and then regenerate the exchangers by leaching or back-extraction with aqueous ammonia or alkylamines. The concept of this approach is that the pH of the feed solution is essentially at or above the $pK_a$ of the carboxylic acid, the $pK_a$ of the anion exchanger (or sorbent, or extractant) is higher than the pH of the feed solution, and the $pK_a$ of the ammonium or alkylammonium is higher than the $pK_a$ of the exchanger, extractant or sorbent. The high volatility of the alkylamine enables decomposition of the highly basic alkylammonium.

Since the $pK_a$ s of typical alkylammonium compounds range from 9 to 11 (trimethylammonium, for example, is 9.8) and the $pK_a$s of typical carboxylic acids of interest range from 3 to 5, we have between 4.8 and 6.8 pH units available as the overall driving force.

This corresponds to a ratio of concentrations of 100,000 to ten million, and is thereby advantageous for the separation process. Of this overall driving force, some fraction (e.g., 2 to 3.5 pH units) will be taken up by the difference between the pH of the feed solution and the $pK_a$ of the carboxylic acid.

DETAILED DESCRIPTION OF THE INVENTION

This process allows carboxylic acids typically having $pK_a$s in the range of 3 to 5 to be directly recovered from fermentation broths and the like which typically have pHs in the range of 4.5 to 7 without pH adjustment so that the acid-depleted broths can be directly recycled. The acid sorption step of the process can be carried out in a zone away from the fermentor. Alternatively, the acid sorption can be carried out within the fermentor itself as long as the fermentor is equipped to admit acid-lean sorbent and to separate and withdraw loaded sorbent.

BRIEF DESCRIPTION OF THE DRAWINGS

In this description of the invention, reference will be made to the accompanying drawings, in which.

DESCRIPTION OF PREFERRED EMBODIMENTS

Figure 1:
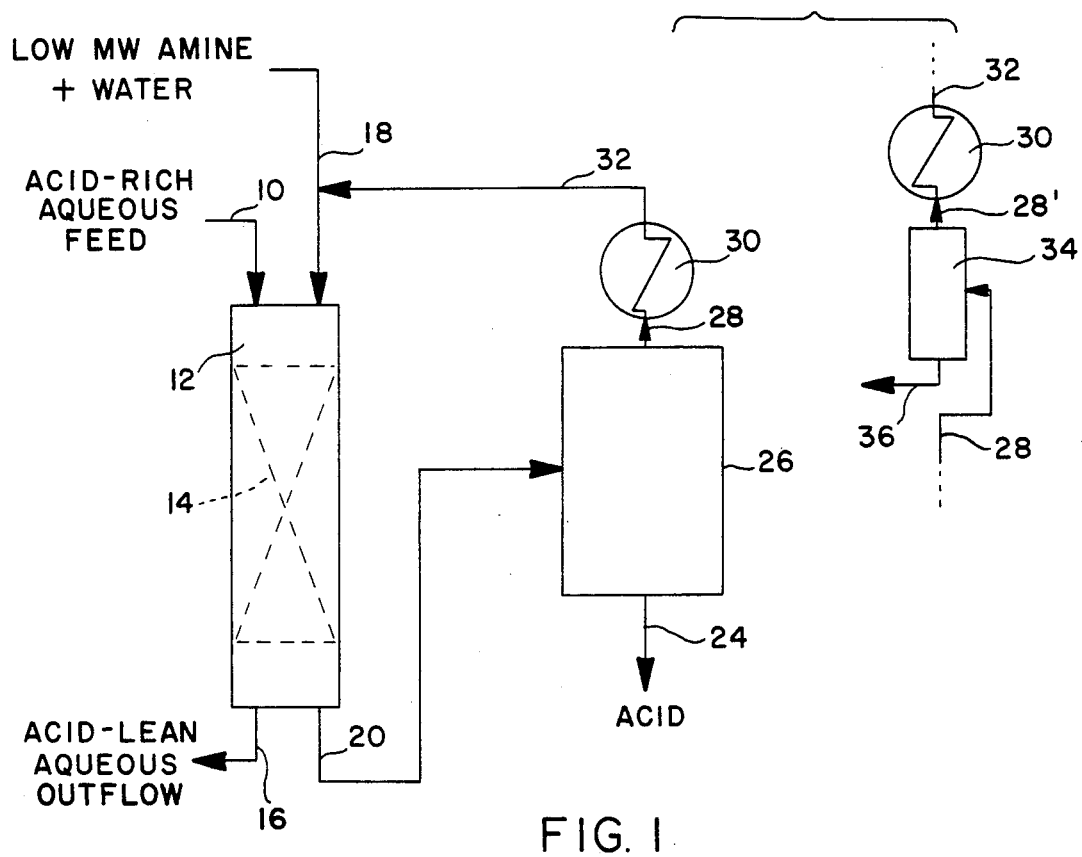
FIG. 1 is a schematic flow diagram illustrating the process of the invention embodied as a solid phase sorption process.

This section is arranged as follows:

First, two representative embodiments of the process of the invention are described with reference to FIGS. 1 and 2.

Then, typical acids which may be recovered by the process are described.

Next, ammonium and low molecular weight amines which may be used in the process are described.

Then, the various acid-sorbing organic phases, including liquid extraction, solid phase and ion-exchange phases, will be discussed.

THE PROCESS

The present invention sorbs carboxylic acids from aqueous solutions at pHs close to or above the acid's $pK_a$ with liquid or solid sorbents. Then it regenerates the carboxylic acid-sorbing solids and organic liquid extractants by contact with aqueous ammonia or low molecular weight alkylamine. This converts the sorbed carboxylic acids directly with ammonia or water-soluble lower alkylamines into aqueous solutions of ammonium or lower alkylammonium carboxylates. These carboxylates are then decomposed and optionally dewatered to yield ammonia or the low molecular weight alkylamine and the carboxylic acid which is recovered. This high pH acid sorption and regeneration process is illustrated as part of an overall solid phase sorption process in FIG. 1. In FIG. 1 an aqueous feed stream such as a pH 6.0 fermentation broth which comprises a water-based solution having from a few parts per million to about saturation of carboxylic acid is fed through line 10 to an ion exchange unit or solid/gel sorption unit 12. Unit 12 contains a bed of solid sorbent 14. The solid phase sorbent can be a strongly basic solid or a weak to moderate basicity ion exchanger. This solid or gel sorbent may be an amine-containing resin or the like so as to adsorb selectively the carboxylic acid groups out of the acid-rich aqueous feed.

Typical pH values giving good fermentor operation for production of carboxylic acids are in the range of 5 to 6 and above, although it is not really possible to generalize (e.g., the fermentation for citric acid operates at a much lower pH). This speaks toward ion exchangers with $pK_a$s in the range of 6 to 8.5, sufficiently higher than the $pK_a$ of the feed solution but sufficiently lower than the $pK_a$ of the aqueous ammonia or alkylamine; or to other sorbents with equivalent basic strength.

Duolite A-340 (a mixed polyethylene diamine/quaternary ammonium sorbent/exchanger, Rohm and Haas Corp.) and Dowex MWA-1 (a tertiary amine sorbent, Dow Chemical Company) retain appreciable capacity for acetic acid ($pK_a = 4.76$) at pH values as high as 6.5 to 7. Thus these resins are suitable representative sorbents.

The contact with the sorbent gives rise to an acid-lean aqueous outflow which is taken out of contactor 12 via line 16 and may be directly recycled to the fermentation zone in light of its high pH. The outflow in line 16 can be suitably monitored until a breakthrough in carboxylic acid level is noted, indicating that the solid sorbent 14 has removed its capacity of carboxylic acid. At this point, feedline 10 is closed via means not shown and aqueous outflow line 16 is also closed. An aqueous solution of ammonia or a low molecular weight alkylamine such as trimethylamine is then fed to contactor 12 via line 18 and contacts the solid sorbing phase 14. This causes the ammonia or low molecular weight trialkylamine to react with the sorbed carboxylic acid and form an ammonium or alkylammonium carboxylate, which is soluble in water and thus carried out of contactor 12 via line 20. This stream is then passed to dewatering-/decomposing zone 26. There, heat and/or reduced pressure are applied so as to remove water and decompose the ammonium or alkylammonium carboxylate into the corresponding ammonia or low molecular weight alkylamine and carboxylic acid. If, as is usually the case, the ammonia or alkylamine is more volatile than the acid, the ammonia or alkylamine can be taken off along with water. The mixture of water and ammonia or low molecular weight alkylamine can be taken overhead via line 28, condensed in condensor 30 and recycled to line 18 via line 32. This overhead mixture can be fractionated, if desired or necessary, to a water stream removed via line 36 and an ammonia or alkylamine-rich stream (line 28') by fractionation column 34 or the like. The ammonia or alkylamine, with whatever accompanying amount of water is present, is condensed in condensor 30 and then recycled through line 32 to line 18 as shown. The acid which is freed by this decomposition and amine removal is removed via line 24.

Although the exact conditions employed will depend in part on the equipment employed and in part upon the volume and exact nature of the feedstock and extractants, the cycle for the feedstock in the first extractor typically ranges from about one minute to about two hours and more typically from about five minutes to about one hour. These residence times can also reflect the rate at which feedstock is passed over the solid sorbing phase. This rate, or linear hourly space velocity (LHSV) can range from about 0.5 to about 60, especially 1 to 12.

It is generally preferred to use a volume of sorbent and a concentration of acid-sorbing material adequate to remove a substantial fraction of the desired carboxylic acid from the aqueous feed. This generally means that the number of equivalents of acid-sorbing groups such as amines or the like present in the acid-sorbing material should exceed or at least equal the number of equivalents of acid present in the volume of aqueous feed passing through the sorbent bed during one contacting cycle.

In the desorbing stage, again, cycle times are typically selected from about one minute to about three hours, although longer times may be used if convenient. Also, it is desirable to use a relatively concentrated solution of ammonia or low molecular weight alkylamine in the desorption. For this purpose, the ammonia or alkylamine may be dissolved under pressure, if desired. It does appear, however, that substantially complete desorption occurs whenever the amount of ammonia or lower alkylamine in equivalents in the aqueous leachant is approximately equal to or greater than the number of equivalents of carboxylic acid being recovered from the sorbent phase. Typically, very complete desorption occurs with from about 1.0 to 1.5 equivalents of ammonia amine based on acid. Although larger amounts of ammonia or the lower alkylamine can be used, it appears that essentially complete recovery of the carboxylic acid is achieved at about this number of molar equivalents. Of course, excesses of ammonia or low molecular weight alkylamine can be used if desired and, if only partial recovery of the carboxylic acid is desired, lower amounts of ammonia or alkylamine material may be used, accordingly.

In the dewatering/decomposition stage 26, the exact amount of water removed can vary up to essentially complete removal of water as needed to free the amine, i.e., to residual water levels of from as low as 1% to say 90%. This stage primarily serves to decompose the carboxylate into the free ammonia or alkylamine and the free acid. As the decomposition progresses, either or both the free acid or the free ammonia or amine is removed, driving the decomposition forward and permitting a more complete decomposition of the carboxylate and recovery of acid. In the embodiment shown in FIG. 1, the amine is taken overhead and removed, and the acid is removed as well.

The dewatering/decomposition step is carried out under relatively mild conditions such as a temperature of from about 20° C. to about 200° C. and particularly 30° to 175° C., an average residence time of from about 1 minute to 3 hours and especially 2 minutes to 2 hours, and a pressure from about 50 torr (vacuum) to about 2 atmospheres. A moving dry gas phase, especially an oxygen-free gas phase, can also be present to assist the dewatering-decomposition.

In determining how much water to remove, the extent to which the salt is decomposed, and the conditions used to effect these processes, one must bear in mind the fact that the free carboxylic acids can react with ammonia or non-tertiary alkylamines (i.e., monoalkylamines or dialkylamines) to give amides. If ammonia or a non-tertiary-alkyl amine is present and is exposed to the carboxylic acid for prolonged periods at elevated temperature, a lower yield may result and amine may be degraded.

Ultimately, the acid should be obtained as free of residual ammonium or alkylammonium carboxylate and contaminating ammonia or alkylamine as possible. This can be facilitated by various washings, crystallizings and the like as needed. Representative levels of carboxylate decomposition range from about 25% up to essentially 100%.

The process of this invention not only works in a solid sorption setting as described with reference to FIG. 1, but also can be employed using a liquid extraction medium. Such a process is shown representatively in FIG. 2. In FIG. 2, again, an acid-rich aqueous feed such as a fermentation broth having a pH close to or above the $pK_a$ of the acid is charged through line 10, this time to a countercurrent contactor 42. A liquid organic extractant is also charged to the contactor via line 44. In the case shown, the organic extractant has a density less than that of water so that the heavier aqueous feed moves down through an ascending stream of organic extractant. The organic extractant is a strongly basic material which has acid-sorbing properties which enable it to preferentially sorb the carboxylic acid out of the aqueous feed. This strongly basic acid-sorbing property may be inherent in the organic liquid but, more commonly, the liquid organic phase contains a strongly basic carboxylic acid-sorbing material (for example, an organic amine extractant). A typical acid-sorber is an alkylamine having a straight chain alkyl long enough to impart predominant partitioning to the organic phase, for example, tri-n-octylamine. When used in fermentation settings, it may be important to select a sorbent phase which does not harm the fermentation organisms. The hazard can be avoided by using a material which is of very low water solubility (i.e., less than a few ppm), and/or removing residual material from the aqueous raffinate before recycle to the fermentor.

Typically, the volume ratio of aqueous feed to acid sorbent fed to contactor 42 during the contacting period will range from about 30:1 to about 1:10, depending, in part, upon the concentration of acid, and to an extent upon the pH of the aqueous solution.

The contacting of the high pH aqueous feed with the acid-sorbing organic liquid extracts the carboxylic acid from the aqueous feed, giving rise to a high pH acid-lean aqueous raffinate which is removed via line 46. The carboxylic acid-rich extract is removed via line 48 to a second counter-current contactor 50. In contactor 50 the acid-rich organic stream is passed upward through a descending stream provided by line 18 of low molecular weight alkylamine or ammonia dissolved in water. The low molecular weight alkylamine or ammonia reacts with the acid present in the organic phase to give rise to a low molecular weight alkylammonium or ammonium carboxylate. This carboxylate is soluble in the water phase and is removed from contactor 50 as the aqueous extract via line 52. The organic raffinate generated by this second extraction includes the organic solvent as well as any strongly basic acid-sorbing material. This regenerated acid-sorber raffinate is removed from contactor 50 via line 54 and may be recycled advantageously to line 44 and reused. The alkylammonium or ammonium carboxylate-containing aqueous stream removed via line 52 is passed to dewatering/decomposing zone 26. As described with reference to FIG. 1, the stream is dewatered and decomposed so as to give rise to a vaporized stream made up of water and alkylamine. This overhead is taken off via line 28 to condensor 30. The condensate from 30 is recycled via line 32 to column 50. Optionally, the overhead from zone 26 is passed via line 28 to fractionation column 34. There it is split to isolate some or all of its water content which is removed via line 36. The ammonia/amine content of the overhead is passed via line 28' to condensor 30 and recycled via line 32. Zone 26 produces a bottom product made up of the recovered carboxylic acid which is removed via line 24.

In the process shown in FIG. 2, the amount of ammonia or lower alkylamine should be selected along the same lines described with reference to FIG. 1. That is, if complete recovery of carboxylic acid is desired, at least about one equivalent of ammonia or low molecular weight alkylamine should be used for each equivalent of acid being recovered. If a lower degree of recovery can be tolerated or is desired, lower amounts of ammonia or alkylamine may also be used.

It is generally preferred to carry out the steps of this process, especially the decomposition/dewatering, in an oxygen-free or reduced-oxygen environment such as an inert gas blanket to minimize decomposition of the amine itself.

Figure 2:
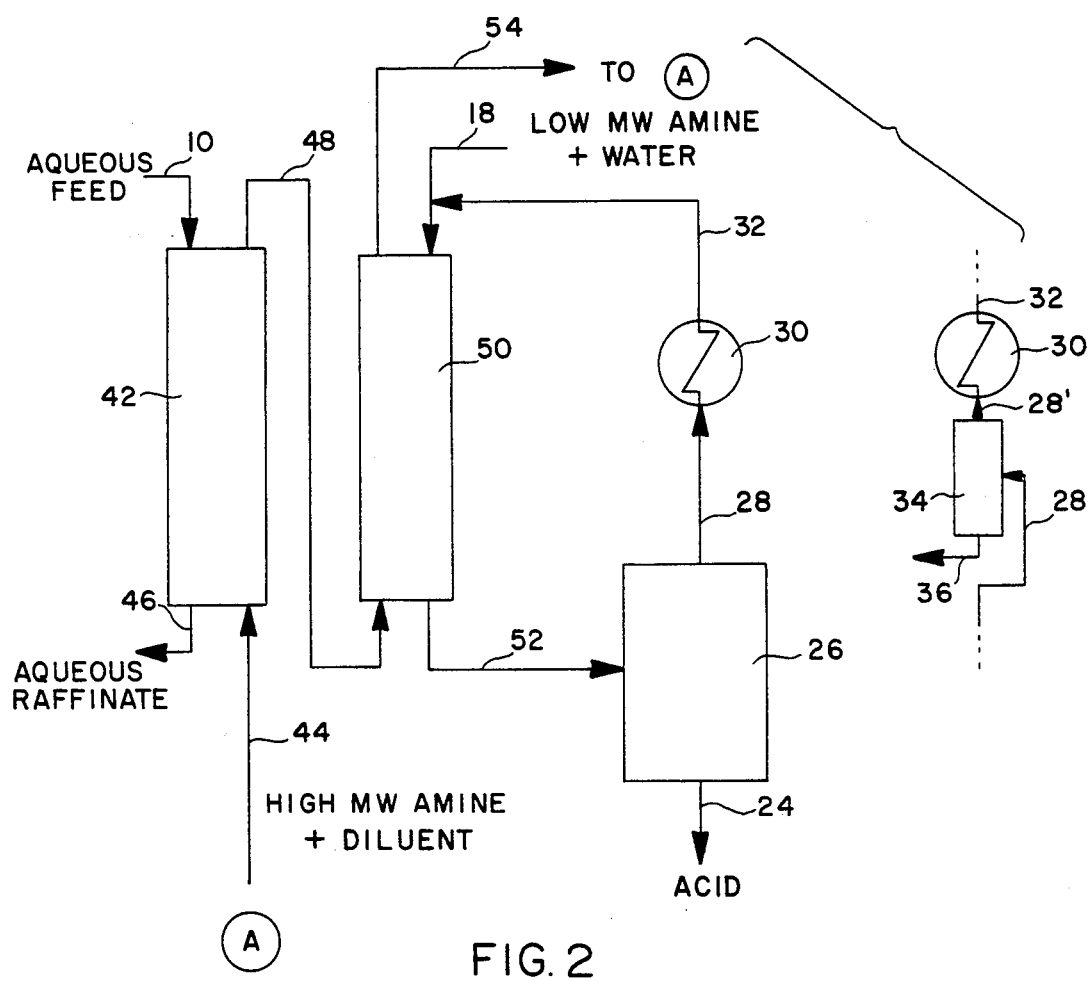
FIG. 2 is a schematic flow diagram of the process of this invention embodied as a solvent extraction process.

The apparatus described with reference to FIG. 2 is merely representative. In place of the countercurrent contactor 42 or countercurrent contactor 50, one can, for example, use one or more mixed vessels and settling zones (phase separation zone), or a cocurrent extractor. The countercurrent contactor itself can be baffled, and can have rotating discs or the like as desired.

The acid recovered via line 24 in either of these processes is typically present as a slurry of solid in aqueous liquid or as a saturated/supersaturated solution of acid. This stream can be further processed to further dewater the acid-containing material, to decolorize it, further remove amine from it and otherwise purify it. These steps are optional.

This process can be practiced in a batch mode, as well, if desired.

The Acids Recovered

The acids isolated and recovered in the process of the invention are carboxylic acids. These acids include aliphatic carboxylic acids of 2–16 carbons and aromatic carboxylic acids of 7–20 carbons. The aliphatic carboxylic acids include 2–16 carbon monoacids such as acetic acid, propionic acid, butyric acid, pentanoic acid, hexanoic acid, octanoic acid, dodecanoic acid and the like. The process is especially effective with polycarboxylic acids such as the di-, tri- and higher carboxyl materials, including the commonly known even-carbon-numbered diacids of 2–12 carbons (that is, the better known dicarboxylic acids of 2, 4, 6, 8, 10 or 12 carbon atoms, such as oxalic acid, succinic acid, sebacic acid, adipic acid and fumaric acid). Of course, the process also works with the odd-numbered acids such as itaconic acid, as well. Lactic acid, malic acid and citric acid are representative hydroxy-containing acids which can be recovered by this process.

The aromatic acids include aromatic monoacids of 7–13 carbons such as benzoic acid, cinnamic acid, phenylacetic acid, naphthoic acid, salicylic acid, and the like, and diacids of 8–12 carbons such as phthalic acid. In addition to the simple oxyhydrocarbon acids, the process can be used to recover those more complex materials such as amino acids, and the like, which are of value and which often occur in aqueous solutions and need to be recovered therefrom. Functional groups such as halogens or nitro groups may be present in the carboxylic acids recovered by the process of this invention.

Since these acids are recovered from solutions having pHs at or above their $pK_a$s, it is helpful to know representative $pK_a$ values. These are shown in Table 1. For diacids, it is the $pK_a$ corresponding to the first ionization constant that is given.

TABLE 1

| $pK_a$ Values for Carboxylic Acids | |
|---|---|
| Acid | $pK_a$ |
| Acetic | 4.8 |
| Adipic | 4.4 |
| Butyric | 4.8 |
| Caprioic | 4.9 |
| Citric | 3.1 |
| Fumaric | 3.0 |
| Lactic | 3.9 |
| Malic | 3.4 |

TABLE 1-continued

| pK$_a$ Values for Carboxylic Acids | |
|---|---|
| Acid | pK$_a$ |
| Propionic | 4.9 |
| Succinic | 4.2 |

These acids are initially present in and recovered from water-based feedstocks having a pH close to or above the acids' pK$_a$s. The term "close to" is defined in the present context to mean a pH not more than 0.2 pH units below the pK$_a$. These feedstocks will contain from about ten parts per million to saturation (for example, up to about 40% by weight) and especially from 0.1% to 25% by weight of recoverable carboxylic acids. The feedstocks can contain a mixture of these acids, in which case the present process can either recover all of the acids or, if differences in forward sorption or back-extractability or leaching with the aqueous ammonia or alkylamine permit, can fractionate the acid mixture. The present invention finds application with prepared feedstocks such as fermentation broths and the like; it also finds application with contaminated aqueous streams. Accordingly, the feedstocks can contain other materials such as salts and organics (sugars, starches, alcohols, aldehydes and the like). Typically, however, these other materials do not substantially follow the carboxylic acids as they are sorbed and back-extracted. Thus, they do not significantly interfere with the process of this invention.

As noted, these acid materials removed and recovered by the process range in size from about 2 carbons (acetic acid) to about 16 carbons and can include monocarboxylic acids, di-and polycarboxylic acids, hydroxycarboxylic acids, and the like. The acid can be aliphatic or aromatic. This wide range of materials spans a range of physical forms: A few of these acids, for example, the 2 to 4 carbon monocarboxylic acids, are relatively volatile liquids.

| | | |
|---|---|---|
| C$_2$ | Acetic Acid | 118° C. b.p. |
| C$_3$ | Propionic Acid | 141° C. b.p. |
| C$_4$ | Butyric Acid | 165° C. b.p. |

Lactic acid is hard to crystallize and usually exists as a concentrated viscous solution. Many of the rest of these acids, especially the dicarboxylic acids, exist as insoluble solids at room temperature. The physical form of the free acids can play a part in the selection of the low molecular weight alkylamine employed in the regeneration.

As noted previously, in the carboxylate decomposition/dewatering steps of the process, a forward driving force is needed to assure substantial conversion of the carboxylate. This driving force typically is provided by separating the free amine from the free acid and removing one or both products from the reaction zone. Preferential vaporization of one product from the other is a very convenient and preferred way to carry out this separation.

The Ammonia or Low Molecular Weight Alkylamine Regenerant

An element of the present invention is the use of an aqueous solution of ammonia or lower alkylamine as the back-extractant (desorbant) material. The alkylamine material is also sometimes referred to herein as a low molecular weight amine or the like.

The regenerant can be an aqueous solution of ammonia—typically a concentrated solution such as containing at least about 2% by weight ammonia.

The low molecular weight alkylamine can be a mono-, di- or trialkylamine. It is selected so that solubility in an aqueous phase is favored. In the extraction/back-extraction embodiment, the lower alkylamine should be selected so as to have a partition coefficient $$\frac{[\text{Concentration in Aqueous Phase}]}{[\text{Concentration in Organic Phase}]}$$

of at least 1, preferably at least 3 and more preferably at least 5. It is also advantageous if the lower alkyl amine has a solubility in the aqueous back-extraction solvent (which is water or water with up to about 10% by volume of lower (1 to 3 carbon) alkanol), of at least about 5% by weight and preferably at least about 10% by weight.

Of these materials, the trialkylamines offer an advantage of not being capable of forming amides with the recovered acids. The mono- and dialkyl materials and ammonia can enter into this irreversible side reaction if prolonged contact with the acid at elevated temperatures occurs.

Another factor to be taken into account in selecting ammonia or an amine is its boiling point relative to the boiling point of the aqueous back-extraction (leaching) solvent and the free acid. If volatilization of the amine is to be used as the mechanism to separate the amine from the acid, a substantial difference in boiling point between them is necessary.

Still another factor to be taken into account in selection of ammonia or an amine is the susceptibility of the amine to thermal decomposition and/or oxidation.

Of the trialkylamines materials, preference is given to trimethylamine for a number of reasons. First, it is the most common and least expensive of these materials. Also, it has a high solubility in water (41 wt% at atmospheric pressure) and thus allows a concentrated back-extract to be formed. Third, it is the most volatile of the trialkylamines (2.9° C. b.p.) and thus, upon decomposition of the trimethylammonium carboxylates, can be removed overhead by distillation with the least amount of heating of the decomposing carboxylate and resulting acid. Other trialkylamines containing up to about 6 or even 8 total carbon atoms—for example dimethylethylamine, methyldiethylamine, triethylamine, dimethyl-n-propylamine, dimethyl-i-propylamine, methyldi-n-propylamine, dimethylbutylamine and the like—may be used. However, they are less volatile and less water-soluble. The one offsetting factor is that they can have higher values of pK$_a$; e.g., pK$_a$=11.0 for triethylamine. Monoalkylamines of up to about 6 carbons such as methylamine, ethylamine, propylamine, butylamine, pentylamine and hexylamine and dialkylamines of up to about 8 total carbons such as dimethylamine, diethylamine, dibutylamine and the like can also be used as can ammonia as long as their potential for side reactions is kept in mind. Mixtures of amines can be used.

In the process of this invention, the ammonia or alkylamine is employed as an aqueous solution (optionally containing up to 10% alkanol). This solution is generally made as concentrated in amine as possible. It can, however, range in concentration from about 1% to saturation, which is about 25%–50% by weight in the case of the more soluble of these amines, such as trimethylamine and about 30% in the case of ammonia. The aqueous solution of ammonia or alkylamine can contain other materials added to improve or facilitate processing. These can include antifoam agents, corrosion inhibitors, and the like, as will be known to those of skill in the art. The ammonia/amine concentration can be increased by dissolving under pressure of up to about 5 or even 10 atmospheres as well.

Solid Sorbent Materials

In a primary embodiment, the carboxylic acid is sorbed onto a solid or gel adsorbent. These materials are either strongly basic adsorbents or ion-exchange resins which would be classed as weak to moderately basic anion exchangers. The solid phase sorbent materials include high surface activity materials such as carbon black, or the like.

The solid sorbents also include weak to moderately basic ion-exchange resins such as pyridyl, pyridinium, amine and ammonium group-containing resins. While defined as "ion exchange" resins it will be appreciated that in many cases these materials are used for their basicity (amine functionality) and not for their ionic exchange potential. These materials include resins with these groups as part of their backbone structure as well as materials which have these groups appended from their backbones. These resin materials are available commercially as basic ion exchange resins. Representative resins are listed in Table 2.

TABLE 2

| Ion Exchange Solid Adsorbents | | |
|---|---|---|
| Commercial Designation | Source | Tyoe of Adsorbent |
| AMBERLITE | | |
| XAD-12 | Rohm & Haas Corp. | Poly (N oxide) |
| XE-309 | Rohm & Haas Corp. | Poly(4-Vinylpyridine) |
| XE-378 | Rohm & Haas Corp. | Poly(2-Vinylpyridine) |
| DOWEX | | |
| WGR | Dow Chemical Company | Epoxy Polymer with Tertiary Amine Groups |
| MWA-1 | Dow Chemical Company | Styrene-Divinylbenzene Copolymer with Tertiary-Amine Groups |
| A-340 | Diamond Shamrock, Inc. | (Duolite) Polyethylene-Diamine, Cross-linked with Epichlorohydrin (a gel-type resin) |
| AG3-X4 | Bio-Rad | Epoxy-amine Polymer with Primarily Tertiary Amine Groups and ~10% Quaternary Groups |
| Reillex 425 402 | Reilly Tar & Chemical Co. | Poly(4-Vinylpyridine) |

Organic Liquid Extractant Materials

When this acid recovery is carried out in a liquid-liquid extraction context, the organic phase into which the acids are extracted is an organic liquid of limited water miscibility. The term "limited water miscibility" is defined to mean that the organic liquid must be capable of forming a second phase when mixed with water and having a maximum water uptake of not more than about 20% by weight of water. This water uptake is based on a two component organic solvent-water system. When used with fermentation broths and the like, it is often helpful to avoid even this level of miscibility and to limit it to 2% or less so as to avoid contaminating the fermentation broth with potentially harmful consequences.

The organic liquid phase can be a single material or it can be a mixture of materials. It should, however, be a material which is a strongly basic extractant. This liquid phase typically includes a solvent. Ketones having 4 to 8 carbons, for example methyl isobutyl ketone, methyl n-butyl ketone, methyl pentyl ketone, diethyl ketone, cyclohexanone, methylcyclohexanone and the like, can be used as solvents. Six to ten carbon alcohols such as n-hexanol, cyclohexanol, heptanol, n-octanol, 2-ethyl hexanol, nonanol, and the like can be used. Four-to 8-carbon ethers such as diethyl ether, methyl butyl ether, methyl pentyl ether, and ethyl butyl ether can also be used. Five to 8 carbon esters such as butyl acetate, pentyl acetate, and the like can be used as well, as can halogenated hydrocarbons, such as chloroform, chloroethane and the like. Aliphatic and aromatic hydrocarbons can be used as well, mixed if necessary with more polar organic compounds in order to engender a single organic phase.

The organic liquid phase usually will also contain up to 80% by weight of an amine or other strongly basic acid sorber to enhance the uptake of acid. This material is optional. Typical amines known to be useful in solvent extraction systems include trialkylamines and tetra alkylamines having at least one 6–12 carbon alkyl group and in total from about 20 to about 36 carbons in their three or four alkyl groups. Such materials include trioctyl/decyl amine, e.g., Alamine 336, (Henkel Corp.), Adogen 363 (Rohm & Haas Corp.) and similar amines marketed by Hoechst, as well as monomethytrioctylammonium chloride (Aliquot 336, Henkel). Other representative tertiary and quaternary amines are listed at pages 92–94 of the text Ritcey, G. M.; Ashbrook, A. W. *Solvent Extraction Principles and Applications in Process Metallurgy,* Part 1 Elsevier, N.Y., 1984 which is incorporated herein by reference. These materials are characterized as being much less soluble in water than the low molecular weight alkylamines which are used to back-extract the acid from the organic phase. Of these, the trialkylamines are preferred.

Preferred organic phases are cyclohexanone, methyl cyclohexanone, methyl isobutyl ketone, and methyl n-butyl ketone, alone or together with up to about 80% by weight of an amine or quaternary ammonium extractant.

Experimental

This invention will be further illustrated by the following Examples.

The three steps of this process—(1) sorption of acid from aqueous solutions at pHs above the $pK_a$; (2) desorption of acid with aqueous amine; and (3) thermal decomposition of the alkylammonium carboxylate were studied.

EXAMPLES 1 AND 2

Sorption of Acid

Resin samples were loaded with succinic acid using the following procedure. One-gram samples of resin were contacted with approximately 10 ml of about 6% by weight succinic acid at various pHs arrived at by addition of sodium hydroxide in a 20-ml scintillation vial. The two phases were equilibrated for at least 48 hours on a shaker bath thermostatted at 25° C. The phases were then separated by centrifugation for 8 minutes at 2000 rpm, and the resin was weighed. The concentrations of acid in the initial and final solutions were determined by adjusting the solution pH to 2.2 using hydrochloric acid, then analyzing the solution by HPLC analysis using a C18 column. The amount of acid on the loaded resin was then determined through a mass balance.

Figure 3:
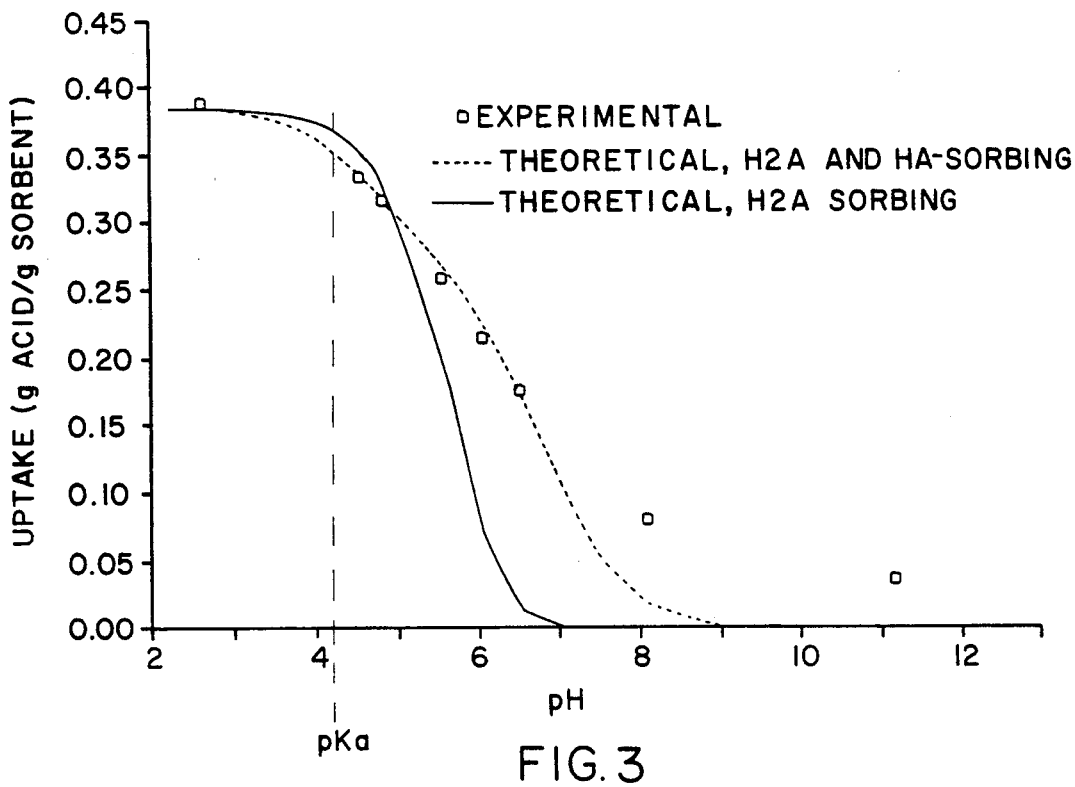
FIG. 3 is a graph illustrating the effect of pH on the sorption of succinic acid onto AG3-X4 sorption resin.
Figure 4:
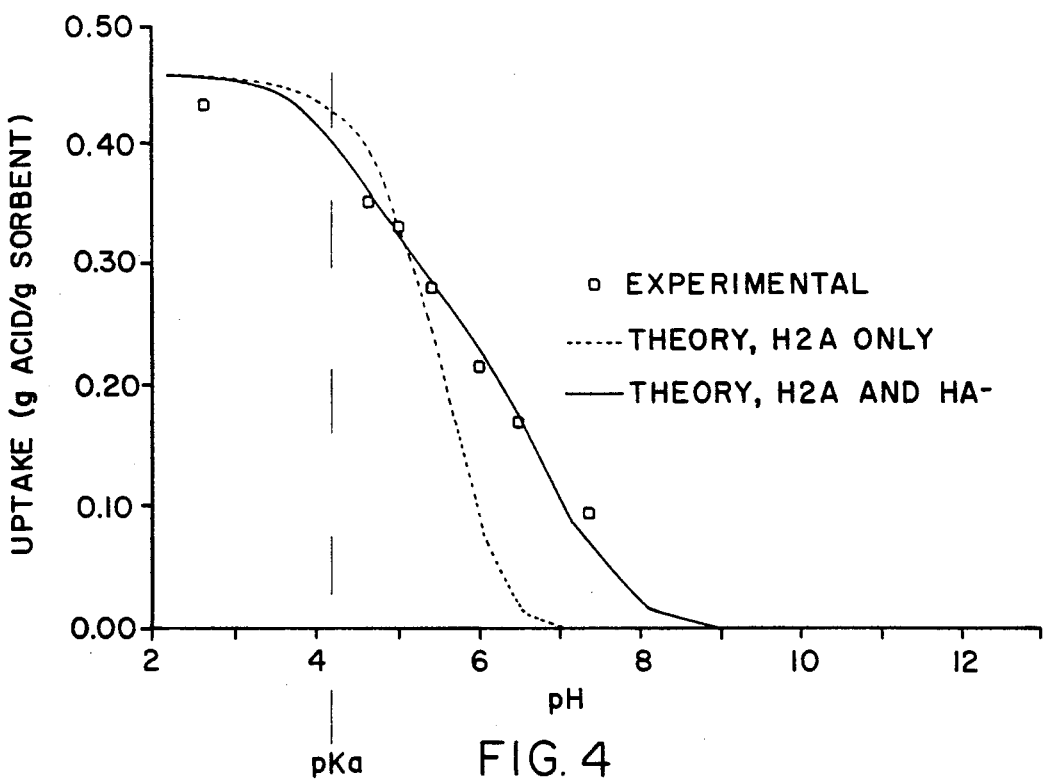
FIG. 4 is a graph illustrating the effect of pH on the sorption of succinic acid onto MWA-1 resin.

Two resins were tested. Bio-Rad AG3-X4 gave the results shown in FIG. 3. Dowex MWA-1 gave the results shown in FIG. 4.

In both cases it was observed that these basic sorbents were able to sorb significant quantities of acid at pHs well above the $pK_a$ of the succinic acid and throughout the range of pHs found in fermentation zones (pH 5–6).

EXAMPLES 3 AND 4

If the experiments of Examples 1 and 2 were repeated using fumaric acid or lactic acid in place of succinic acid, similar results would be attained.

EXAMPLES 5 AND 6

Desorption Experiments

One gram resin samples loaded with succinic acid were contacted with 13 ml of aqueous trimethylamine (TMA) in a scintillation vial. The two phases were again equilibrated for 48 hours on a shaker bath at 25° C. The phases were then separated by centrifugation and the resin weighed. The concentration of TMA in the initial solution was determined by adding a sample to an excess of 1N hydrochloric acid, then titrating to pH 5.0 with sodium hydroxide. The concentration of acid in the aqueous phase was obtained by HPLC analysis using a C18 column. The concentration of acid remaining on the sorbent was determined by leaching the resin with 1N hydrochloric acid, then analyzing the leachate by HPLC. A mass balance on the acid closed within the experimental error.

Results of Leachings using the Procedures

Figure 5:
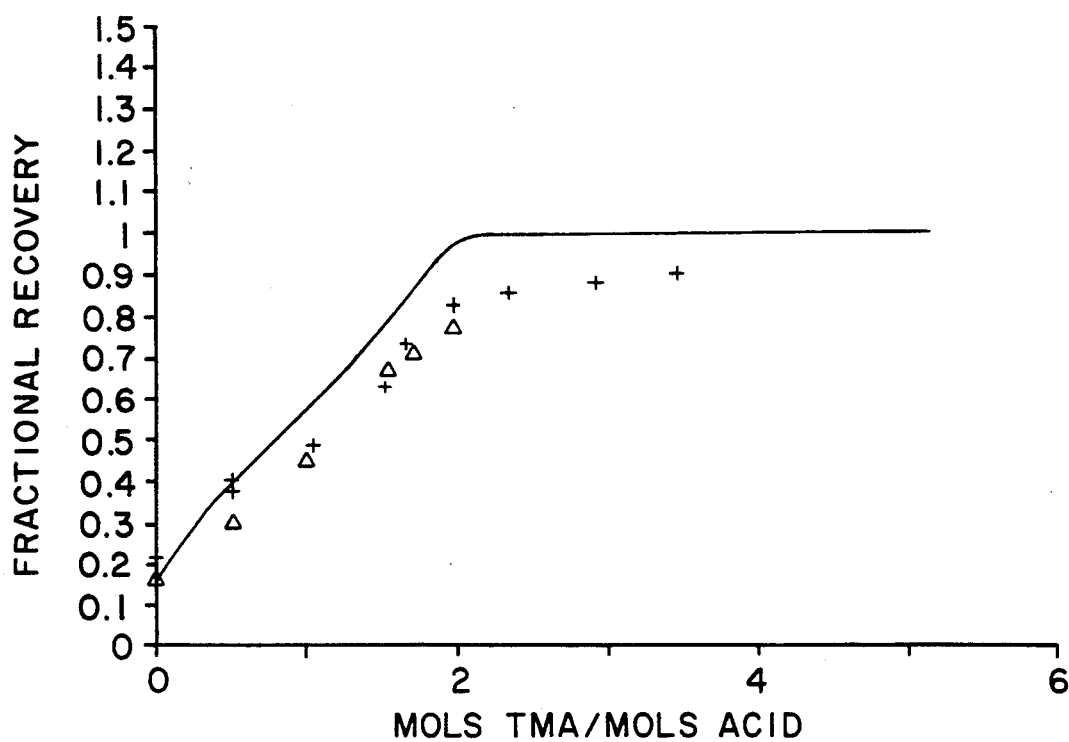
FIGS. 5 and 6 are graphs illustrating the acid recovery possible from the resins of FIGS. 3 and 4 using aqueous trimethylamine to regenerate.
Figure 6:
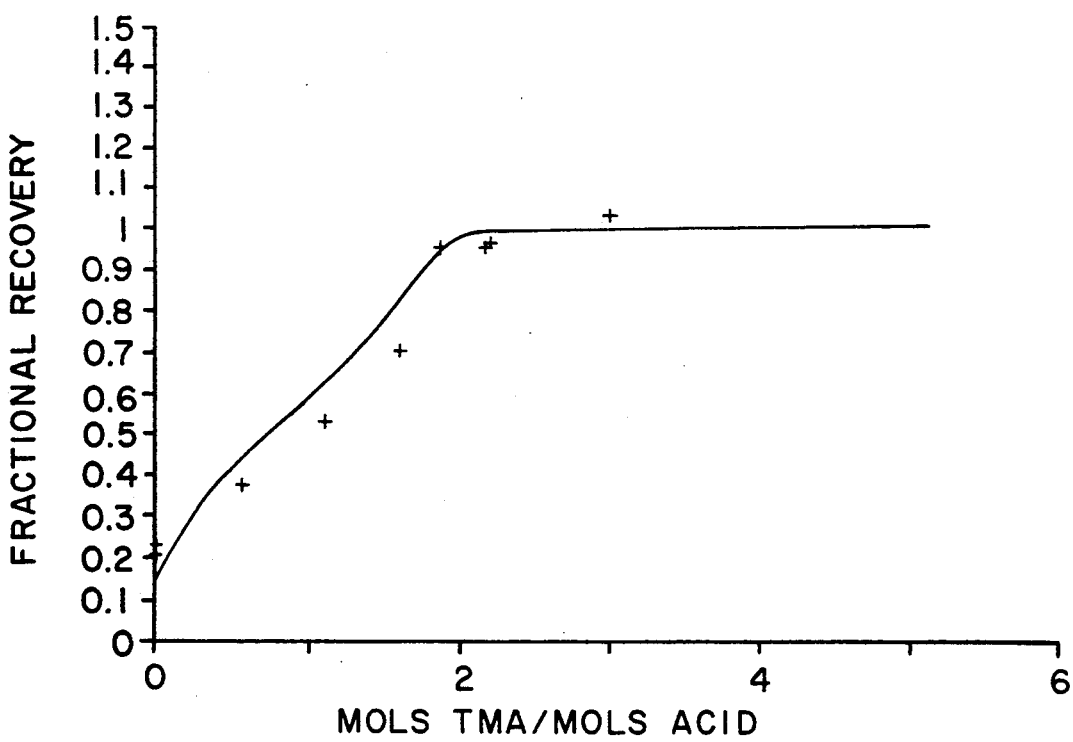

Results for the leaching of succinic acid from the two different adsorbents used in Examples 1 and 2 (Bio-Rad AG3-X4 and Dowex MWA-1) are shown in FIGS. 5 and 6. For MWA-1, essentially 100% of the acid was leached into the aqueous phase at conditions in which the molar ratio of TMA to acid was at least 2:1. For AG3-X4, a recovery of 87% of the acid was achieved at a 2:1 molar ratio. The curves shown are theoretical curves generated from the chemical-equilibrium and mass-balance equations that describe the system. The data fit reasonably well to these curves.

EXAMPLES 7 AND 8

If the experiments of Examples 5 and 6 were repeated using lactic acid-loaded resin or fumaric acid-loaded resin, similar results to those achieved in Examples 5 and 6 would be achieved.

EXAMPLES 9-11

Thermal Decomposition Experiments

Aqueous solutions of trimethylammonium carboxylates produced to simulate the materials generated in Examples 5–8 were heated under nitrogen to prevent possible oxidation of the TMA.

The aqueous solution (60 ml) was placed in a three-neck 100-ml round-bottom flask operated under vacuum and equipped with a magnetic stir bar and a heating mantle. Water driven off from the solution was condensed in condenser and collected in a graduated cylinder. Most of the TMA evolved was collected in an absorber flask containing dilute $H_2SO_4$.

Nitrogen was bubbled through the aqueous trimethylammonium carboxylate solution. A vacuum (to 350–380 mm Hg absolute) was pulled on the reaction train.

The temperature of the aqueous trimethylammonium carboxylate solution was allowed to increase gradually, reflecting the increase in boiling temperature of the solution, until a point was reached when most of the water had been removed. At this point, a sharp increase in temperature was observed. Heating was adjusted to keep the temperature below 130° C.

At the end of the run, a sample of the water collected was titrated with 0.03N $H_2SO_4$ in order to determine the TMA content. For total pressure in the range 350 to 380 mg Hg, less than 2% of the total TMA was present in the water. A sample of the final absorber solution was titrated with 0.01N or 0.1N NaOH.

The moles of TMA and the volume of water collected versus time and the nitrogen flow rate were used to determine the partial pressures of water vapor and TMA as functions of both temperature and the concentrations of salt and free acid in solution.

After the trimethylammonium carboxylate salt was concentrated and thermally decomposed as described above, there remained behind a light yellow mixture of carboxylic acid and residual water and TMA (probably in the form of the trimethylammonium carboxylate). In the cases of fumaric and succinic acids, crystals of the acid were present. These acids were removed and purified.

Lactic Acid. As an aqueous solution of lactic acid is concentrated by heating, crystalline lactic acid does not precipitate. Instead, the viscosity of the solution increases steadily as self association of the acid occurs.

In the thermal regeneration experiments carried out with aqueous solutions of trimethylammonium lactate, the goal was therefore to remove essentially all the TMA, leaving behind a concentrated aqueous solution of lactic acid and lactic acid polyesters, similar to the commercial syrup. When 45 mL of 1.6N lactic acid and 1.89N TMA in water was heated at 101°–120° C. and 300 mm Hg for 28 hours, only 63% of the water and 62% of the TMA present in the initial aqueous solution were removed, leaving behind a viscous aqueous solution. The increasing ratio of lactic acid to TMA, without precipitation of the highly soluble acid, would serve to depress the volatility of the residual TMA. Also, formation of intermolecular esters in concentrated solutions may impose severe transport limitations, hampering further TMA removal. The removal of TMA could be enhanced by addition of an appropriate solvent, e.g., methyl isobutyl ketone, and continued evaporation.

Figure 7:
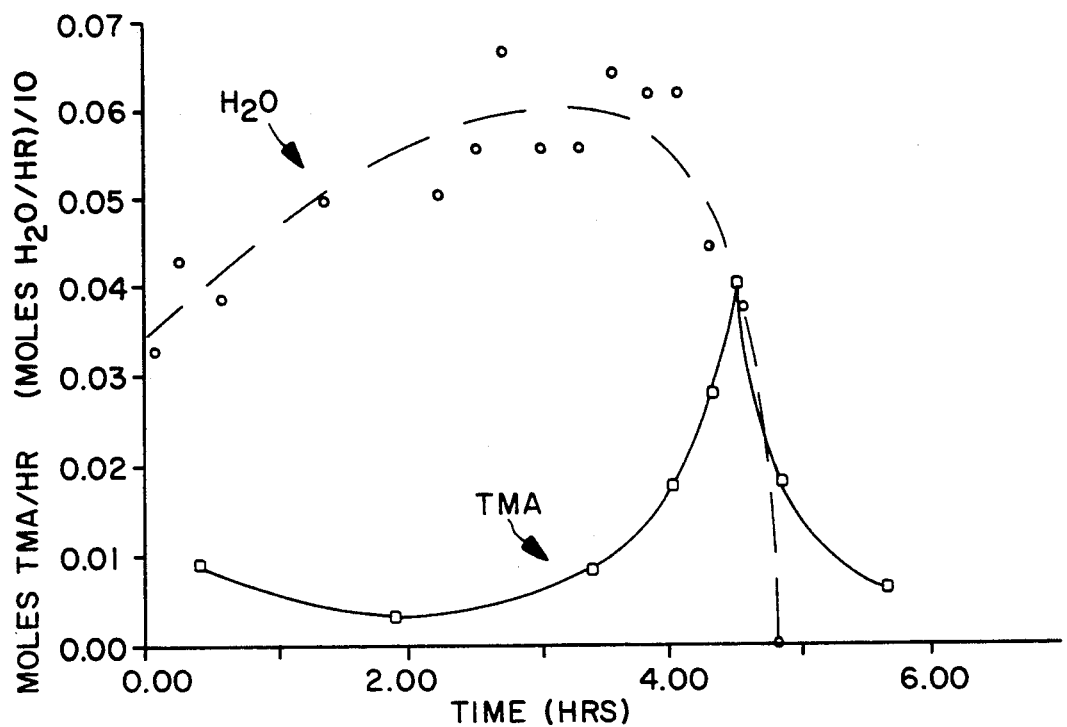
FIG. 7 is a graph showing rates or removal of water and trimethylamine during dewatering/decomposition of a trimethylammonium succinate salt solution.
Figure 8:
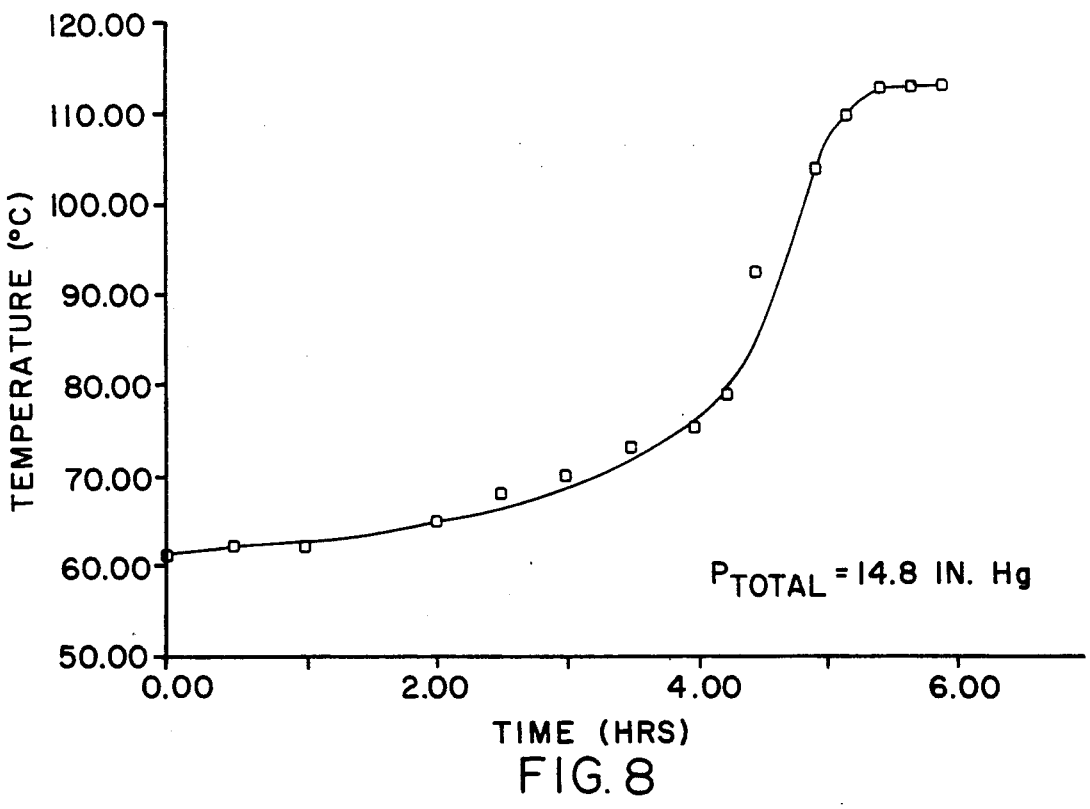
FIG. 8 is a time/temperature curve for the dewatering/decomposition experiment described in FIG. 7.

Succinic Acid and Fumaric Acid. FIG. 7 shows the rates of water and TMA removal from an aqueous solution initially containing 2.0 moles TMA/mole succinic acid. FIG. 8 shows the corresponding solution temperature, which initially corresponds to the rising boiling point of the solution. At the end of the run, the temperature is held constant at 112° C.

Despite its volatility, TMA is initially held in solution due to complexation by the acid. The trimethylammonium carboxylate is decomposed when a high enough temperature is reached, a high enough concentration is reached, and/or as crystallization of the acid occurs, driving the decomposition reaction. TMA is released after most of the water has been removed. The extra release of TMA at the start of the run resulted from a slight excess of TMA in the initial aqueous solution.

Similar experiments were carried out with aqueous solutions of the di-trimethylammonium salt of fumaric acid. As with succinic acid, the TMA is released after most of the water is removed, and again an end-product containing the acid in crystalline form is obtained.

EXAMPLES 12-14

The sorption experiment of Example 1 could be repeated using a liquid phase extractant in place of the solid resin and varying the acid among lactic, succinic and fumaric.

Equal volumes of an aqueous solution of the acid would be contacted with a solution of 0.3M Alamine 336 in MiBK to extract the acid into the organic phase. The pHs vary above and below the $pK_a$ of the acid.

After the contacting, each phase is removed by pipet. The pH of the aqueous phase is measured. The amount of acid remaining in the aqueous phase would be determined by HPLC. The concentration of acid in the organic phase can also be determined. These extractions would show that substantial fractions of these acids can be extracted at pHs of 5, 6 or higher.

EXAMPLES 15-17

Back-Extraction Experiments

Back-extractions from MiBK-Alamine 336 solution produced as in Examples 12-14 into aqueous trimethylamine (TMA) were carried out at 25° C. in a separatory funnel with an organic to aqueous phase ratio of 8/3 (v/v). The two phases were then transferred to erlenmeyer flasks. The flasks were placed at 25° C. in a shaker bath for two days to allow the phases to settle. The phases were separated by pipet.

GC analysis of the organic phase was used to determine the extent to which TMA had been transferred to the organic phase. For the aqueous phase, the concentration of acid was determined by HPLC analysis.

The concentration of acid remaining in the organic phase was determined by HPLC analysis of an aqueous NaOH extract of the organic phase. The NaOH extract was obtained by contacting a 5 ml sample of the organic phase with an excess of aqueous NaOH in a centrifuge tube. The two phases were mixed with a magnetic stir bar and then centrifuged for 30 minutes at 2000 rpm to separate the phases.

For all three acids, essentially 100% of the acid was back-extracted into the aqueous phase at conditions in which there was at least one mole of TMA for every equivalent weight of acid. This is a sign that the basicity of aqueous TMA ($pK_b = 4.1$) is much stronger than that of the organic amine.

In the back-extraction experiments, the equilibrium concentration of TMA in the organic phase was less than 0.0005 wt. %, as long as the overall molar ratio of TMA to acid was less than or equal to that corresponding to stoichiometric equivalence. This presumably reflects full ionization and pairing of the TMA with the acid in the aqueous phase.

When TMA was present in excess of the stoichiometric ratio, partitioning of TMA into the organic phase was substantially greater. Representative organic-phase concentrations of TMA were 2.5, 1.4 and 0.55 wt. % for 2.1 moles TMA/mole lactic acid, 3.1 moles TMA/mole succinic acid, and 3.0 moles TMA/mole fumaric acid, respectively. Pearson and Levine (1952) report the partition coefficient of uncomplexed TMA into MIBK from water (wt. fraction basis) to be 1.88.

What is claimed is:

1. A process for recovering carboxylic acid from a carboxylic acid-containing aqueous feedstream having a pH close to or above the $pK_a$ of the acid comprising:
   (a) contacting the carboxylic acid-containing feedstream at a pH close to or above the $pK_a$ of the acid with an acid-sorbing phase selected from a strongly basic sorbent, a strongly basic extractant and a weak to moderate-basicity anion exchanger under conditions whereby carboxylic acid is sorbed from the feedstream to the acid-sorbing phase, thereby forming an acid-depleted aqueous feedstream and an acid-enriched acid-sorbing phase;
   (b) separating the acid-depleted aqueous feedstream from the acid-enriched acid sorbing phase;
   (c) contacting the separated acid-sorbing phase with an aqueous solution of low molecular weight alkylamine or ammonia, thereby solubilizing said carboxylic acid from the sorbing phase into said aqueous solution as alkylammonium or ammonium carboxylate, and forming a carboxylic-acid lean acid-sorbing phase;
   (d) separating the aqueous solution of alkylammonium or ammonium carboxylate from the acid-lean acid-sorbing phase;
   (e) treating the aqueous solution of alkylammonium or ammonium carboxylate to decompose the alkylammonium or ammonium carboxylate to yield the carboxylic acid and the alkylamine or ammonia; and
   (f) recovering the carboxylic acid yielded in step (e).

2. The process of claim 1 wherein the acid-containing feedstream is a fermentation broth from a fermentation zone.

3. The process of claim 2 wherein the acid-depleted aqueous feedstream generated in step (a) is an acid-depleted fermentation broth which is ultimately recycled to the fermentation zone at a pH above the $pK_a$ of the acid.

4. The process of claim 1 wherein in step (c) ammonia is present.

5. The process of claim 1 wherein in step (c) low molecular weight alkylamine is present.

6. The process of claim 5 wherein in step (c) the alkylamine is a trialkylamine.

7. The process of claim 6 wherein the trialkylamine is trimethylamine.

8. The process of claim 5 wherein in step (e) said treating comprises dewatering and removing the alkylamine.

9. The process of claim 1 wherein the acid-sorbing phase is a strongly basic sorbent.

10. The process of claim 1 wherein the acid-sorbing phase is a strongly basic extractant.

11. The process of claim 1 wherein the acid-sorbing phase is a weak to moderate basicity anion exchanger.

12. The process of claim 1 wherein the $pK_a$ of the acid is from about 3.8 to about 5.0 and wherein the pH of the feedstream is from about 0.2 units lower to about 4 units higher than said $pK_a$.

13. The process of claim 12 wherein the acid is selected from lactic, fumaric, succinic, malic, adipic, itaconic, benzoic and salicylic.

14. The process of claim 13 wherein the acid-containing feedstock is a fermentation broth from a fermentation zone.

15. The process of claim 14 wherein the acid-depleted aqueous feedstream generated in step (a) is an acid-depleted fermentation broth which is recycled to the fermentation zone at a pH close to or above the $pK_a$ of the acid.

16. A process for recovering carboxylic acid from a carboxylic acid-containing aqueous feedstream having a pH close to or above the $pK_a$ of the acid comprising:
(a) contacting the carboxylic acid-containing feedstream at a pH close to or above the $pK_a$ of the acid with an acid-sorbing phase selected from a strongly basic sorbent, a strongly basic extractant and a weak to moderate-basicity anion exchanger under conditions whereby carboxylic acid is sorbed from the feedstream to the acid-sorbing phase, thereby forming an acid-depleted aqueous feedstream and an acid-enriched acid-sorbing phase;
(b) separating the acid-depleted aqueous feedstream from the acid-enriched acid sorbing phase;
(c) contacting the separated acid-sorbing phase with an aqueous solution of trimethylamine, thereby solubilizing said carboxylic acid from the sorbing phase into said aqueous solution as trimethylammonium carboxylate, and forming a carboxylic-acid lean acid-sorbing phase;
(d) separating the aqueous solution of trimethylammonium carboxylate from the acid-lean acid-sorbing phase;
(e) treating the aqueous solution of trimethylammonium carboxylate to decompose the trimethylammonium carboxylate to yield the carboxylic acid and the trimethylamine; and
(f) recovering the carboxylic acid yielded in step (e).

17. The process of claim 16 wherein the acid-containing feedstream is a fermentation broth from a fermentation zone.

18. The process of claim 17 wherein the acid-depleted aqueous feedstream generated in step (a) is an acid-depleted fermentation broth which is ultimately recycled to the fermentation zone at a pH above the $pK_a$ of the acid.

19. The process of claim 18 wherein the acid-sorbing phase is a strongly basic sorbent.

20. The process of claim 18 wherein the acid-sorbing phase is a strongly basic extractant.

21. The process of claim 18 wherein the acid-sorbing phase is a weak to moderate basicity anion exchanger.

22. The process of claim 18 wherein the $pK_a$ of the acid is from about 3.8 to about 5.0 and wherein the pH of the feedstream is from about 0.2 units lower to about 4 units higher than said $pK_a$.

23. The process of claim 22 wherein the acid is selected from lactic, fumaric, succinic, malic, adipic, itaconic, benzoic and salicylic.

24. The process of claim 23 wherein the acid-containing feedstock is a fermentation broth from a fermentation zone.

25. The process of claim 24 wherein the acid-depleted aqueous feedstream generated in step (a) is an acid-depleted fermentation broth which is recycled to the fermentation zone at a pH close to or above the $pK_a$ of the acid.

* * * * *